United States Patent [19]

Rittner et al.

[11] Patent Number: 5,152,875
[45] Date of Patent: Oct. 6, 1992

[54] SEPARATION OF M- AND P-DICHLOROBENZENE

[75] Inventors: Siegbert Rittner, Mörfelden-Walldorf; Adolf Schmidt, Hofheim am Taunus; Rudolf Steiner, Erlangen-Kosbach; Leonhard Unverdorben, Uttenreuth, all of Fed. Rep. of Germany

[73] Assignee: Hoechst Aktiengesellschaft, Frankfurt am Main, Fed. Rep. of Germany

[21] Appl. No.: 681,891

[22] Filed: Apr. 8, 1991

[30] Foreign Application Priority Data

Apr. 10, 1990 [DE] Fed. Rep. of Germany ....... 4011501

[51] Int. Cl.$^5$ .......................... B01D 3/34; C07C 25/08
[52] U.S. Cl. ......................... 203/48; 203/60; 203/91; 570/211
[58] Field of Search ............... 203/48, 57, 60, 91, 203/DIG. 21; 570/211

[56] References Cited

U.S. PATENT DOCUMENTS

| | | | |
|---|---|---|---|
| 2,541,682 | 2/1951 | Arnold | 203/48 |
| 3,220,933 | 11/1965 | Amir et al. | 203/60 |
| 3,847,755 | 11/1974 | Chanel et al. | 203/57 |
| 4,300,004 | 11/1981 | Wissner et al. | 203/48 |
| 4,488,937 | 12/1984 | Berg et al. | 203/60 |
| 4,676,872 | 6/1987 | Berg et al. | 203/60 |

FOREIGN PATENT DOCUMENTS

| | | |
|---|---|---|
| 2332889 | 9/1975 | Fed. Rep. of Germany . |
| 54-160322 | 12/1979 | Japan . |
| 58-174333 | 10/1983 | Japan . |
| 0772080 | 12/1981 | U.S.S.R. ............... 570/211 |

Primary Examiner—Virginia Manoharan
Attorney, Agent, or Firm—Connolly and Hutz

[57] ABSTRACT

A process for separating m- and p-dichlorobenzene by extractive rectification with an extractant and removal of this extractant. Using as extractant an alkylene carbonate of the formula

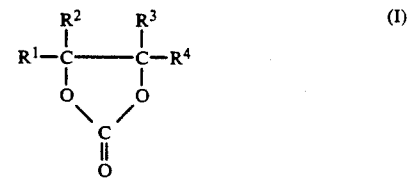

where $R^1$, $R^2$, $R^3$ and $R^4$ are identical to or different from one another and each is hydrogen, methyl or ethyl, with the proviso that together the radicals $R^1$ to $R^4$ do not contain more than 6 carbon atoms.

The process of the invention makes it possible to separate off the m-isomer in high purity.

13 Claims, No Drawings

SEPARATION OF M- AND P-DICHLOROBENZENE

DESCRIPTION

The present invention relates to a process for separating m- and p-dichlorobenzene by extractive rectification with an extractant.

The isolation of m-dichlorobenzene (m-DCB) from mixtures with o- and p-dichlorobenzene (p-DCB) is one of the most difficult separating problems in the chemistry of aromatic intermediates. This is because the boiling points of m- and p-DCB are less than 0.2° C. apart, so that the removal of more than 99% pure m-DCB by fractional rectification is virtually impossible.

Because of this separating problem, even very indirect routes are occasionally accepted in industry to obtain at least almost 98% pure m-DCB. For instance, a process is described in Winnacker/Küchler, Chemische Technologie, 4th edition, volume 6, page 158 (1982), whereby m-dichlorobenzene is prepared specifically via m-dinitrobenzene or m-chlorobenzenesulfonyl chloride. U.S. Pat. No. 3,170,961 recommends the route via bromo isomers whereby the dichlorobenzenes are brominated, the bromo isomers are separated by distillation and the bromine is then split off in such a manner as to get back the original dichlorobenzenes. However, this process is difficult and costly. Similarly, a melt crystallization as employed successfully for separating many aromatic isomers is uneconomical for m-/p-DCB mixtures, since the crystallization of pure m-DCB requires low temperatures (about −30° C.) and very high concentrations of more than 88% of m-DCB in the feed mixture and gives a high-percentage strength eutectic mixture of 88% m-DCB.

Since m-DCB is a commercially important intermediate for a number of important products, there has always been great interest in methods for isolating it. For instance, a method involving the use of molecular sieves is described in U.S. Pat. No. 2,958,708. However, this inherently interesting process, which meets the desired m-DCB purities of above 99%, has the disadvantage of the considerable problems associated with the regenerating of molecular sieves, and is very expensive.

A particularly attractive separating technique from the practical aspect is considered to be the technique of extractive rectification, which involves the use of extractants as specific assistants to obtain very pure m-DCB.

For instance, hexamethylphosphoramide, a carcinogenic substance, is said in DE U.S. Pat. No. 2,332,889 to be usable as such an assistant. Other extractants mentioned therein as effective on the basis of the separating factor (the relative volatility) in the ternary system are dimethyl sulfoxide, N-methylpyrrolidone and dibutyl sulfoxide. Furthermore, Japanese Patent Applications JP-A 54 160 322 and JP-A 58 174 333 recommend inter alia such assistants as o-, m- and p-cresol and aniline derivatives. However, these substances are more or less toxic, they have a corrosive effect, or their boiling points are unfavorable. Moreover, some of these substances are not very thermostable or their thermal long-term stability is not sufficient, so that they cannot be used repeatedly, as would be important however for practical purposes.

The object therefore is to provide a process for separating m- and p-dichlorobenzene which is free of the disadvantages of the prior art, which in particular uses a toxicologically and ecologically safe, thermostable and non-corrosive extractant, and which makes it possible to isolate the m-isomer in a purity of above 99%. Furthermore, this extractant shall have a higher boiling point than the mixture to be separated and be an easily meterable, non-viscous and inexpensive liquid.

It has now been found that alkylene carbonates, such as ethylene carbonate and propylene carbonate, are highly suitable for this purpose.

The present invention accordingly provides a process for separating m- and p-dichlorobenzene by extractive rectification with an extractant and removal of this extractant, wherein the extractant used is an alkylene carbonate of the formula I

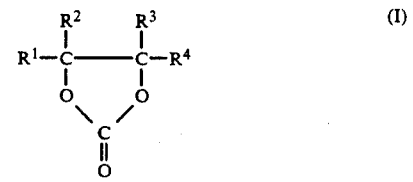

therefor. Where $R^1$, $R^2$, $R^3$ and $R^4$ are identical to or different from one another and each is hydrogen, methyl or ethyl, with the proviso that together the radicals $R^1$ to $R^4$ do not contain more than 6 carbon atoms.

According to the invention, it is possible to obtain m-DCB distillates of almost 100% purity not only from m-/p-DCB mixtures having a high m-DCB content but also, surprisingly, for example from mixtures which contain only 50% of m-DCB, as obtained for example in the catalytic isomerization of other dichlorobenzenes. Of course, separation of a mixture which contains only 50% of m-DCB requires a column with a higher number of separating stages than if the feed mixture contains 80% of m-DCB. In addition to these two DCB isomers the isomer mixture may also contain other chlorinated benzenes and/or chlorinated nitrobenzenes in small amounts. These compounds are in general monochlorobenzene, ortho-dichlorobenzene and trichlorobenzene, which are obtained in the production of dichlorobenzene.

The extractants used are alkylene carbonates of the formula (I), for example ethylene carbonate, propylene carbonate or butylene carbonate. Particular preference is given to ethylene carbonate and propylene carbonate, whose boiling points are sufficiently but not too different from those of m- and p-dichlorobenzene. It is also possible to use mixtures thereof.

To show the effectiveness of the extractants used according to the present invention, the table below shows measured values of the efficiency $\beta$, i.e. the factor by which the separating factor (the relative volatility) of m-dichlorobenzene is raised compared with p-dichlorobenzene. These measured values were obtained at 120° C. with 10% by volume of each isomer present in the extractant. For comparison, the table also includes the corresponding values for hexamethylphosphoramide and sulfolane.

TABLE

| Extractant | Efficiency $\beta$ |
| --- | --- |
| Hexamethylphosphoramide | 1.22 |
| Sulfolane | 1.16 |
| Ethylene carbonate | 1.17 |

TABLE-continued

| Extractant | Efficiency β |
| --- | --- |
| Propylene carbonate | 1.19 |

The efficiency β was measured using the gas-chromatographic vapor method as described earlier in Verfahrenstechnik 8 (1974), No. 12, pages 343–347.

The tests showed that ethylene carbonate and propylene carbonate are as efficient as the toxic and thermally unstable hexamethylphosphoramide and the excessively high-boiling, odor-intensive sulfolane.

For this reason and because of their other positive material properties, largely determined for the first time for the purposes of this invention (non-corrosive and chemically and thermally stable even on prolonged use, readily separable from dichlorobenzenes and so on), and not least also because of their non-toxicity, these carbonates are highly suitable for use as extractants for an extractive rectification of m-/p-dichlorobenzene mixtures.

Advantageously, the process of the present invention is carried out by operating the extraction column at a low pressure, preferably at about 50 to about 300 hacto Pascal (Hpa), in particular at about 80 to about 150 hPa, measured at the top of the column, with a very small pressure loss between column base and column top, preferably about 0 to about 100 hPa, in particular about 10 to about 70 hPa, and with a very large number of separating stages, preferably at least about 20 to about 250, in particular at least about 80 to about 180, theoretical separating stages. The reflux ratio (reflux:distillate) is advantageously about 2:1 to about 30:1, in particular about 4:1 to about 25:1, and the feed ratio between the feed rate of extractant and the feed rate of m-/p-DCB mixture is preferably about 4:1 to about 40:1, in particular about 9:1 to about 30:1. In general, the mixture fed into the extraction column for separation has a temperature which, depending on the chosen pressure, is generally between 60° and 150° C., preferably between 70° and 120° C., in particular between 75° and 115° C. The temperature of the extractant is likewise within these ranges and in general is equal to that of the mixture to be separated. The temperature at the base of the extraction column should advantageously not exceed 180° C., preferably 160° C.

In a preferred embodiment, the extractive rectification of the present invention is combined with a melt crystallization. This is because, if the m-isomer is desired as a particularly pure product, it can be economical to use extractive rectification to produce an m-DCB distillate which still contains from 2 to 7% of p-DCB and in a downstream, single-stage melt crystallization is separated into 100% pure m-DCB crystallizate and a eutectic melt (88% of m- and 12% of p-DCB) and then to return this melt into the extractive rectification. For example, 1,000 kg of a distillate which contains 950 kg of m-DCB and 50 kg of crystalline p-DCB can be made to yield 580 kg of 100% pure m-DCB. The remaining melt of 420 kg (88% of m-DCB) is returned into the extractive rectification.

EXAMPLES

1. A laboratory column 50 mm in internal diameter which is equipped with a vacuum jacket, mirrored on the inner surface, heated from the outside, which is packed with SULZER laboratory packing EX and which has an effective separating height of 3.50 m is charged at a height of 1.00 m with the mixture to be separated, consisting of 87.5% of m-, 2.5% of p- and 10.0% of o-dichlorobenzene, at a temperature of 75° C., and at a height of 3.50 m with the extractant propylene carbonate, likewise at a temperature of 75° C., and the reflux. The pressure at the top of the column is 100.0 hPa. The extractant leaves the vaporizer at the base of the column almost quantitatively (99.8% of the feed) in a boiling liquid state together with a little m-dichlorobenzene and virtually the entire amount of impurity comprising p- and o-dichlorobenzene, while m-dichlorobenzene is withdrawn at the top of the column in vapor form contaminated with only 0.2% of p-dichlorobenzene and 3% of readily removable propylene carbonate. The reflux vapor condensate obtained at the top of the column is set to 7.2 g/min, which corresponds to a reflux:distillate ratio of 9:2, while the mixture to be separated and the propylene carbonate are fed in at rates of 2.00 g/min and 28.00 g/min respectively and distillate and bottom product are produced at rates of 1.60 g/min and 28.40 g/min respectively.

2. The same column as described in Example 1 is charged at a height of 1 m with another mixture consisting of 50.4% of m- and 49.6% of p-dichlorobenzene and at a height of 3.5 m with propylene carbonate and the reflux. The pressure at the top of the column is again 100.0 hPa, and the temperature of the mixture to be separated and the extractant is 105° C. The reflux ratio of reflux: distillate is 9:1, while the feeds of 2.00 g/min of mixture to be separated and 28.00 g/min of propylene carbonate are turned into 0.95 g/min of distillate and 29.05 g/min of bottom product. The distillate contains 91.3% of m- and 5.7% of p-dichlorobenzene and also 3.0% of propylene carbonate.

Removing the extractant from the bottom product is not difficult and is usually carried out in a downstream column, so that the extractant, freed from low boilers, can be fed back into the extraction column. On the basis of the examples it is possible to calculate to what extent the effective separating height of the column must be increased to obtain a more than 99% pure m-product.

3. The same column as described in Example 1 is extended for a further run by two further lengths of column of the same type as the existing lengths to a total of 5.00 m of effective separating height. The column is fed at a level of 1.00 m with the mixture to be separated, consisting of 70.0% of m-, 29.8% of p- and 0.2% of o-dichlorobenzene, at a level of 4.00 m with the extractant propylene carbonate and at a level of 5.00 m with the reflux. The mixture to be separated is fed in at a temperature of 95° C. and at a rate of 2.00 g/min, while the extractant is fed in at 95° C. and 45.00 g/min. The reflux is introduced at 75° C. and 20.0 g/min. The reflux ratio is 9:1. The top of column pressure is 100.0 hPa. The rectification at a top of column vapor temperature of 8° C. gives 1.12 g/min of distillate containing 99.2% of m-dichlorobenzene. The bottom product is obtained at 155° C. at a rate of 45.88 g/min and consists of 98% of propylene carbonate and 2% of dichlorobenzenes.

4. The same column as described in Example 1 is charged at a level of 1.00 m with a mixture of 72.9% of m- and 27.1% of p-dichlorobenzene at a rate of 2.0 g/min, while 20 g/min of ethylene carbonate is introduced at a height of 3.00 m and the vapor condensate reflux is introduced at the top of the column. The pressure at the top of the column is 100.0 hPa. The reflux ratio of reflux: distillate is 11:1, producing 1.3 g/min of distillate consisting 94.5% of m-, 4.2% of p-dichlorobenzene and 1.3% of ethylene carbonate. The bottom product stream withdrawn from the vaporizer at a rate of 20.7 g/min consists predominantly of the ethylene carbonate extractant, which can be separated from the traces of m-and p-dichlorobenzene by simple thermal regeneration.

What is claimed is:

1. An extractive rectification process for separating a feed mixture consisting of m- and p-dichlorobenzene in an extraction column with an extractant and removal of this extractant, which consists essentially of using as extractant an alkylene carbonate selected from the group consisting of ethylene carbonate, propylene carbonate, butylene carbonate and mixtures thereof, and obtaining the m-dichlorobenzene as overhead product and the extractant and p-dichlorobenzene as bottoms product.

2. The process of claim 1, wherein the alkylene carbonate is ethylene carbonate.

3. The process of claim 1, wherein the alkylene carbonate is propylene carbonate.

4. The process of claim 1, wherein the extraction column is operated at a top of column pressure of about 50 to about 300 hPa, with a pressure loss between the base and top of the column from 0 to about 100 hPa and with at least 20 theoretical separating stages.

5. The process of claim 1, wherein the extraction column is operated at a top of column pressure of 80 to 150 hPa.

6. The process of claim 1, wherein the extraction column is operated with a pressure loss between the base and top of the column from 10 to 70 hPa.

7. The process of one claim 1, wherein the extraction column has 80 to 180 theorectical separating stages.

8. The process of claim 1, wherein the extraction column is operated within reflux ratio of 2:1 to 30:1.

9. The process of claim 1, wherein the reflux ration is 4:1 to 25:1.

10. The process of claim 1, wherein the ratio of extractant feed rate to the feed rate for the m-/p-dichlorobenzene mixture is 4:1 to 40:1.

11. The process of claim 1, wherein the ratio of extractant feed rate to the feed rate for the m-/p-dichlorobenzene mixture is 9:1 to 30:1.

12. An extractive rectification process for separating a feed mixture consisting of m- and p-dichlorobenzene with an extractant and removal of this extractant, which consists essentially of using as extractant an alkylene carbonate selected from the group consisting of ethylene carbonate, propylene carbonate, butylene carbonate and mixtures thereof; obtaining the m-dichlorobenzene as overhead product and the extractant and p-dichlorobenzene as bottoms product; operating the extraction column at a pressure of 80 to 150 hPa, with a pressure loss between the base and top of the column from 10 to 70 hPa and with at least 80 theoretical separating stages and combining the extractive rectification with a melt crystallization.

13. An extractive rectification process for separating a feed mixture consisting of m- and p-dichlorobenzene with an extractant and removal of this extractant, which consists essentially of using as extractant an alkylene carbonate selected from the group consisting of ethylene carbonate, propylene carbonate, butylene carbonate and mixtures thereof; obtaining the m-dichlorobenzene as overhead product and the extractant and p-dichlorobenzene as bottoms product and combining the extractive rectification with a melt crystallization.

* * * * *